United States Patent
Pagedas

[19]

[11] Patent Number: 6,045,566

[45] Date of Patent: Apr. 4, 2000

[54] MORCELLATER

[76] Inventor: Anthony C. Pagedas, 8401 W. Edgerton Ave., Greendale, Wis. 53129

[21] Appl. No.: 09/234,917

[22] Filed: Jan. 21, 1999

[51] Int. Cl.$^7$ .................................................... A61B 17/32
[52] U.S. Cl. ........................................... 606/167; 606/114
[58] Field of Search .................................... 606/114, 110, 606/113, 127, 151, 167, 170; 128/898

[56] References Cited

U.S. PATENT DOCUMENTS

| | | | |
|---|---|---|---|
| 4,611,594 | 9/1986 | Grayhack et al. | 606/114 |
| 5,064,428 | 11/1991 | Cope et al. | 606/127 |
| 5,190,561 | 3/1993 | Graber | 606/127 |

*Primary Examiner*—Michael Buiz
*Assistant Examiner*—Kevin Truong
*Attorney, Agent, or Firm*—Ryan Kromholz & Manion, S.C.

[57] ABSTRACT

A morcellater having at least one cutting structure rotatably coupled to a motor mechanism. The cutting structure having a protective structure circumjacent thereto. The protective structure being slidably coupled a housing structure wherein at least a portion of the motor mechanism is located. The invention further including a method of using a morcellater in a body cavity through an incision made therein and wherein the morcellater includes at least one grinding structure, coupled to a motor mechanism, and a protective structure located circumjacent to the grinding mechanism. The protective structure having at least a first end coupled a housing structure wherein at least a portion of the motor mechanism is located and a second free end wherein the grinding structure is generally located. The first end able to freely, upon the application of a predetermined level of pressure to the free end, slide into and out of the housing at least a predetermined distance; the method including. Applying the free end of the protective structure against a target tissue mass. Applying sufficient force to cause the first end to slide into the housing a predetermined distance. Engaging the grinding structure with the target tissue. Actuating the motor mechanism to cause the grinding mechanism to grind up the target tissue sufficiently to allow its removal from the body cavity through the incision.

14 Claims, 6 Drawing Sheets

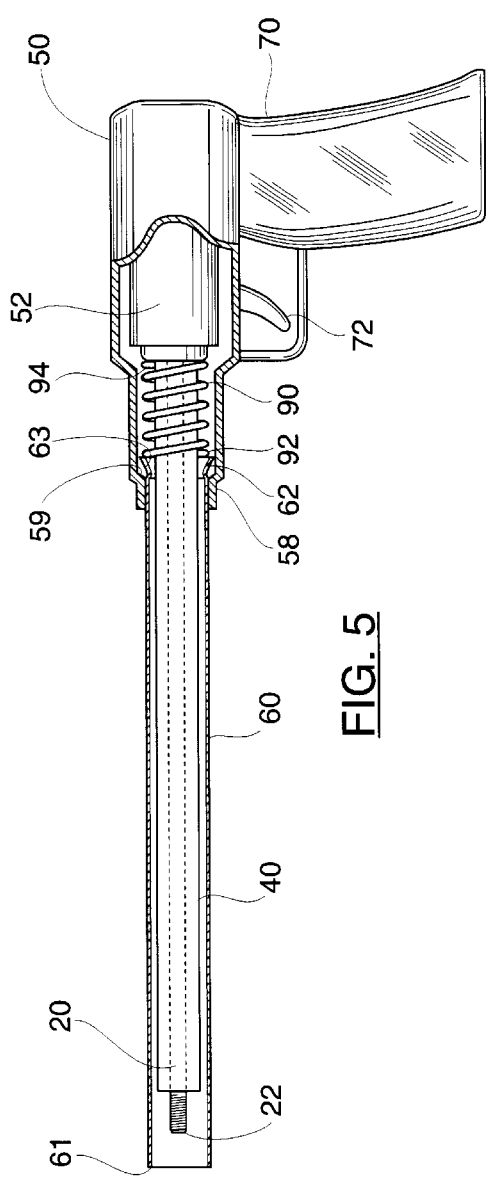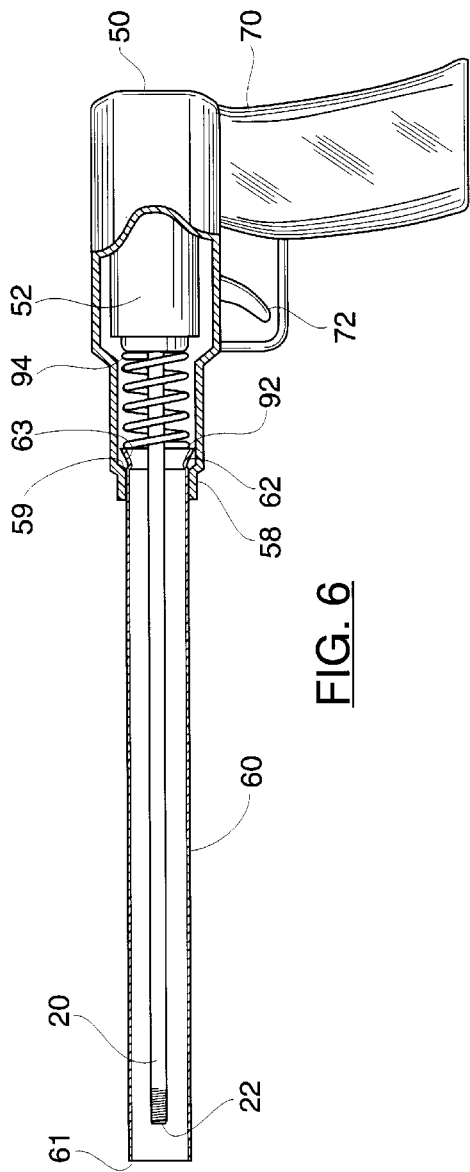

MORCELLATER

BACKGROUND OF THE INVENTION

The present invention generally relates to surgical equipment and specifically to surgical tools used in laproscopic or similar types of surgery. In recent years, the applications for lapraoscopic surgery have expanded to include many different procedures. A benefit of lapraoscopic operations is the relatively quick recovery period experienced by patients, due to the small incisions that are made in the body. These incisions reduce the trauma and the required healing compared to traditional surgery. Lapraoscopic tubes and sleeves with diameters on the order of 10 millimeters are inserted in the body cavity, although the diameter may increase or decrease depending upon the instrument used or the need. Various instruments and a video camera are typically directed through lapraoscopic sleeves for performing and monitoring the surgical steps.

A particular concern in lapraoscopic surgery is the transporting of tissues and other masses that are cut away or retrieved during a surgery. While moving, manipulating, or cutting up a removed mass within the body cavity, pieces of infected or cancerous mass, blood, bile, and other liquids may escape into the body cavity and pose infection problems or other complications. These materials are desirably removed by placing them in a bag or similar enclosure within the body cavity before removal to minimize the risk of infection or other complications. It is important that the containment of the materials be accomplished as quickly as possible with minimal disturbance to the surgical site.

Instruments with membranes or bags have been designed in an attempt to avoid the complications associated with the removal of tissue during lapraoscopic surgery. These devices typically fall into two categories, those that have a bag coiled around an introducing rod that must be unfurled by various maneuvers, and those that pop open a bag using a spring, wire, or other mechanism. A device that falls into the second category is a pouch disclosed in Pagedas (U.S. Pat. No. 5,368,597), which utilizes a flexible rod slidably, connected to a wand to create a reclosable pouch. When the rod bows out, the bag is opened. When the rod straightens, the bag is closed to form a seal.

Typically when a bag is used to contain the tissue or other material that is to be removed through the small incision, it is necessary to first use a morcellater to reduce the size of the tissue mass so that it can fit through the small incision. Accordingly, the top portion of the bag is removed from the body cavity through one of the small incisions. The top portion of the bag is then opened so that the morcellater may be extended into the bag and into contact with the tissue or other material that is to be reduced in mass. A problem is that specimen bags may be ruptured by the use of known morcellating instruments. Additionally, known morcellating instruments are so powerful that they can quickly and inadvertently cut through healthy tissue, bone, or even the operating table.

For the foregoing reasons, there is a need for a morcellater that allows for efficient reduction of the targeted tissue material but will not easily rupture or cut through the bag or other nontargeted tissue material.

Additionally, there is a need for a morcellater with built in fail safe devices that cause the morcellater to automatically turn off if the surgeon operating the device is inadvertently bumped in a crowed operating theater or if the surgeon were to go into seizure from a heart attack or other physical malady.

The present invention is believed to address these and other problems by the unique and simple structures and methods disclosed herein.

SUMMARY OF THE INVENTION

The present invention is a morcellater. At a minimum it is believed preferable that the invention comprise at least one cutting structure coupled to a motor mechanism. The cutting structure may be coupled to allow it to rotate but it should also include a protective structure located circumjacent to it. The protective structure should coupled a housing structure wherein at least a portion of the motor mechanism is located and preferably should be able to slide into and out of the housing at least a predetermined distance.

Optionally the present invention may also include at least one biasing element. Further, the motor mechanism may have a plurality of speeds that it is possible for an operator, like a surgeon to vary between.

Also, the protective structure may be substantially cylindrical and include a proximate end that slidably extends through at least one opening in the housing. The proximate end and the biasing element may be engaged so that the biasing element, a spring or other suitable element is biased against the proximate end. Typically, the biasing element will include a first end biased against the proximate end and a second end biased against the motor.

Additionally, the protective structure may include at least one distal end having at least one opening. The cutting or grinding structure capable of being extended a predetermined distance through the opening.

The morcellater may also include a drive shaft having a first end coupled to the motor and a second end coupled to the cutting structure. The morcellater may further include a drive cylinder located circumjacent to the drive shaft.

Also, the morcellater may include a switching mechanism coupled to the motor. The motor being actuated and controlled by the switching mechanism. The switching mechanism may include a first "off" position and a second "off" position as well as at least one or more "on" position. All the "on" positions located between first "off" position and the second "off" position.

Alternatively, the present invention may be described as method of using a morcellater in a body cavity through an incision made therein. The morcellater having at least one cutting or grinding structure, coupled to a motor mechanism and a protective structure located circumjacent to it. The protective structure having at least a first end coupled a housing structure wherein at least a portion of the motor mechanism is located and a second free end wherein the grinding structure is located. Preferably the first end is able to freely, upon the application of a predetermined level of pressure to the free end, slide into and out of the housing at least a predetermined distance. The method including the steps of applying the free end of the protective structure against a target tissue mass. Applying sufficient force to cause the first end to slide into the housing a predetermined distance. Engaging the grinding structure with the target tissue and actuating the motor mechanism to cause the grinding mechanism to grind up the target tissue sufficiently to allow its removal from the body cavity.

DESCRIPTION OF THE DRAWINGS

FIG. 5 is a cut away side view of the present invention.

FIG. 6 is a cut away side view of an alternative embodiment of the present invention.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 4:
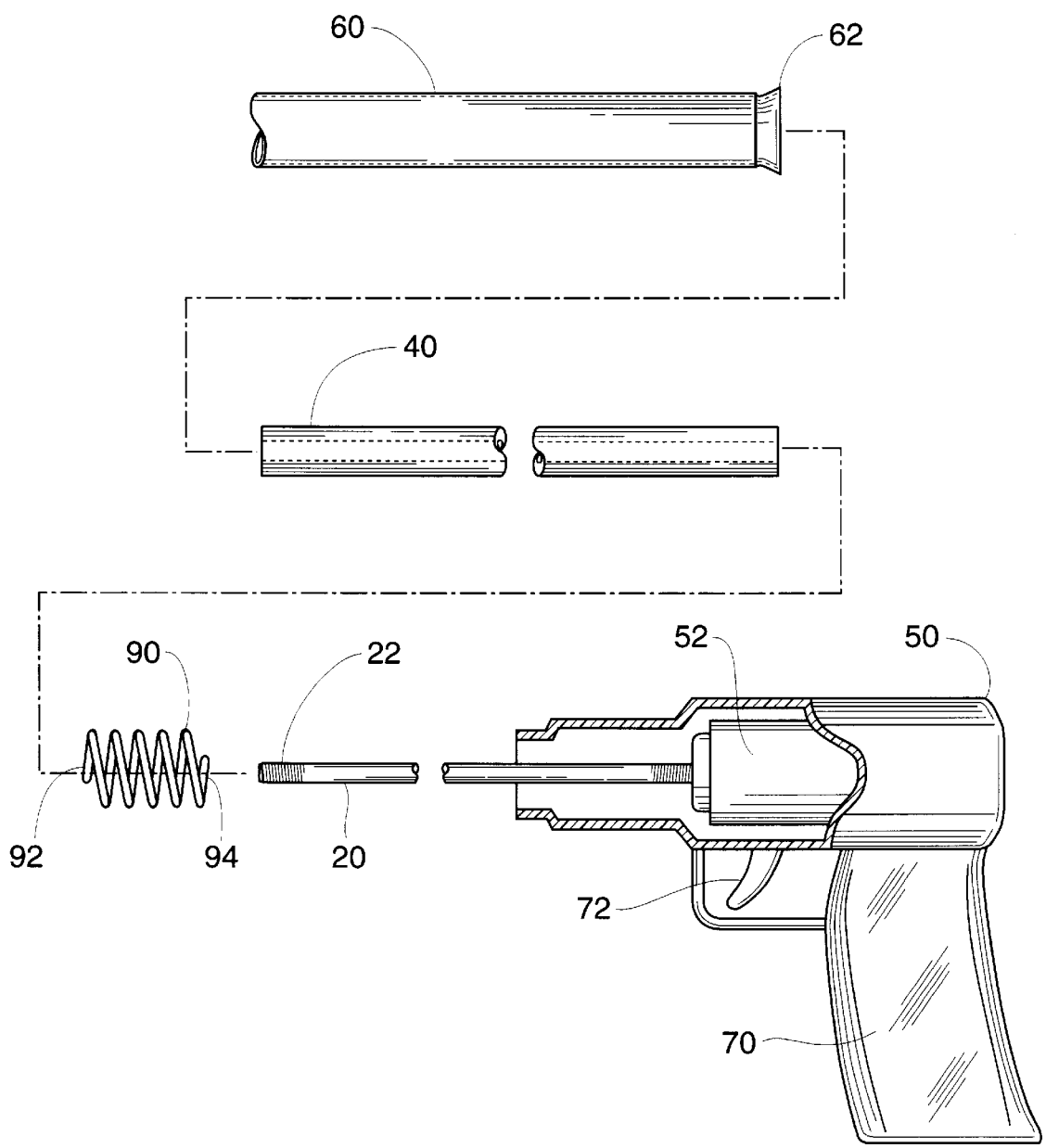
FIG. 4 is an exploded view of the preferred embodiment of the present invention showing the inter-relationship of all component parts.

Referring to FIG. 4, the morcellater 10 of the present invention may be seen to be comprised of a drive shaft 20, a cutting hub 30, a drive cylinder 40, a motor housing 50, and a protective shield 60. The motor housing is coupled to a handgrip 70. A motor 52 is located within the housing 50. The motor 52 is operatively coupled to a trigger mechanism 72. The motor 52 is actuated by manually depressing the trigger mechanism 72. The motor 52 is automatically disengaged by releasing the trigger mechanism 72 or by fully depressing the trigger mechanism 72.

Still referring to FIG. 4, the drive shaft 20 has two threaded ends 22 and 24. The motor 52 includes a threaded opening 54. The drive shaft 20 may be coupled to the motor 52 by engaging threaded end 24 with threaded opening 54. Preferably, a drive cylinder 40, having an opening 42 extending therethrough, is freely mounted onto the drive shaft 20 by extending the drive shaft 20 through the opening 42. A spring 90 may be slid over the drive cylinder 40 so that it is circumjacent thereto.

The biasing element is the spring 90. While a simple coiled spring is shown it should be understood that any appropriate type of biasing element could be used. Accordingly, the invention as with all elements described in the detailed description, should not be limited to nor should the claims, which follow, be limited to the specific structure disclosed. Rather the elements defined in the claims should be interpreted broadly. For example, the term spring should include all devices capable of deflecting so as to store energy, used to absorb shock or as a source of power or to maintain pressure between contacting surfaces. Possible suggestions for alternatives include, without limitations, air cylinders, shock absorbers, leaf springs, volute springs, etc.

The spring 90 has a first end 92 and a second end 94. Second end 94 is preferably in engagement with the motor 52 while first end 92 is in engagement with the clip 62 of the protective shield 60. Clip 62 being snap fit or engaged with receptacle 58 of motor housing 50. Protective shield 60 being circumjacent to both the drive cylinder 40 and the drive shaft 20. Protective shield 60 being slidably engaged with receptacle 58 so that end 63 may slide toward the motor 52 if spring 90 is compressed. Clip 62 engaging with shoulder 59 to prevent shield 60 from inadvertently falling out of receptacle 58. Accordingly, the expansive force of the spring 90 should be sufficient to keep the clip 62 and shoulder 59 abutting one another unless the spring 90 is compressed. Additionally clip 62, preferably, will remain in abutment with shoulder 59 unless or until an ejecting force greater than the expansive force of the spring 90 is applied to the protective shield 60 causing the clip 62 to snap past shoulder 59 thereby removing the protective shield 60 from receptacle 58.

Figure 7:
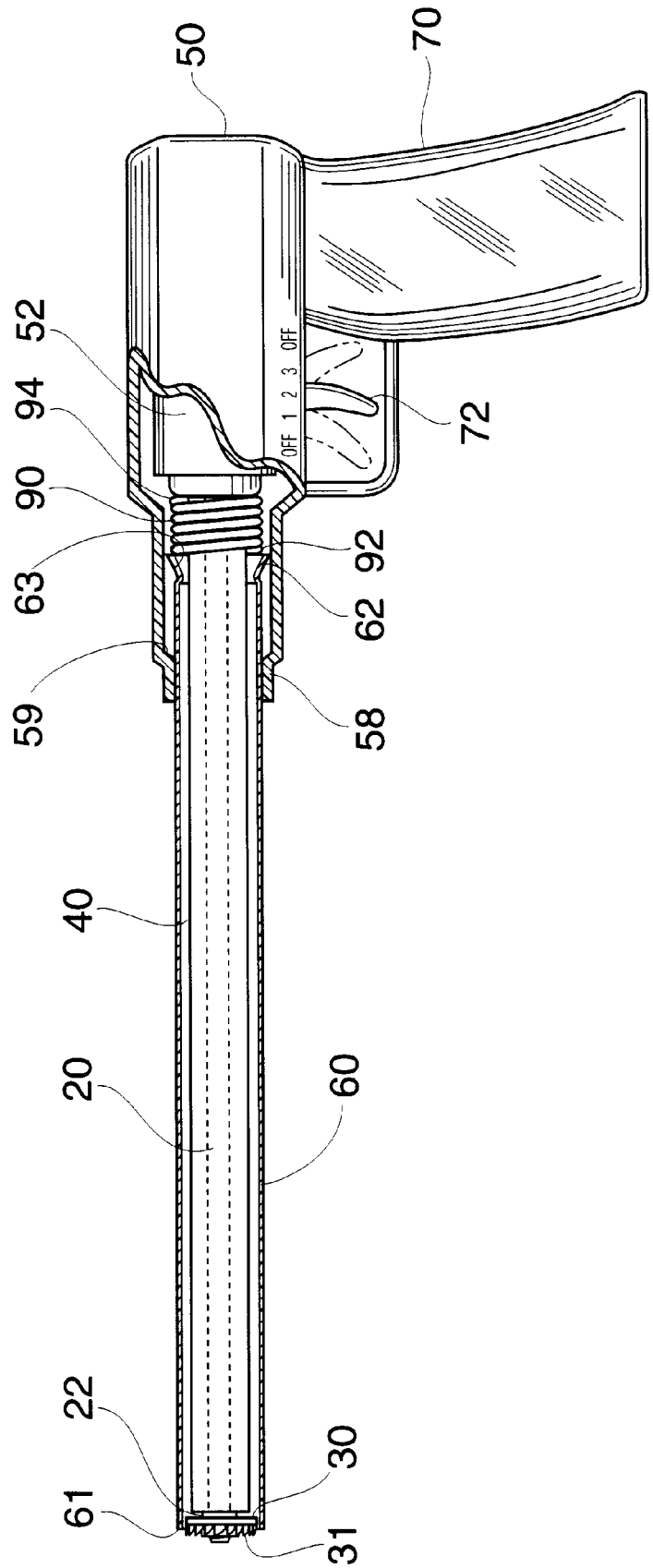
FIG. 7 is a cut away side view of the present invention in which the biasing element is compressed.

Referring now to FIGS. 5 and 7 the cutting hub 30 is mounted onto the threaded end 22 of the drive shaft 20. (See FIG. 7). The protective shield 60 is biased by spring 90 to extend well past the threaded end 22 of the drive shaft 20. The protective shield 60 when retracted and spring 90 is compressed, as shown in FIG. 7, exposes just enough of the cutting hub 30 to sufficiently engage the tissue material 18.

Figure 1:
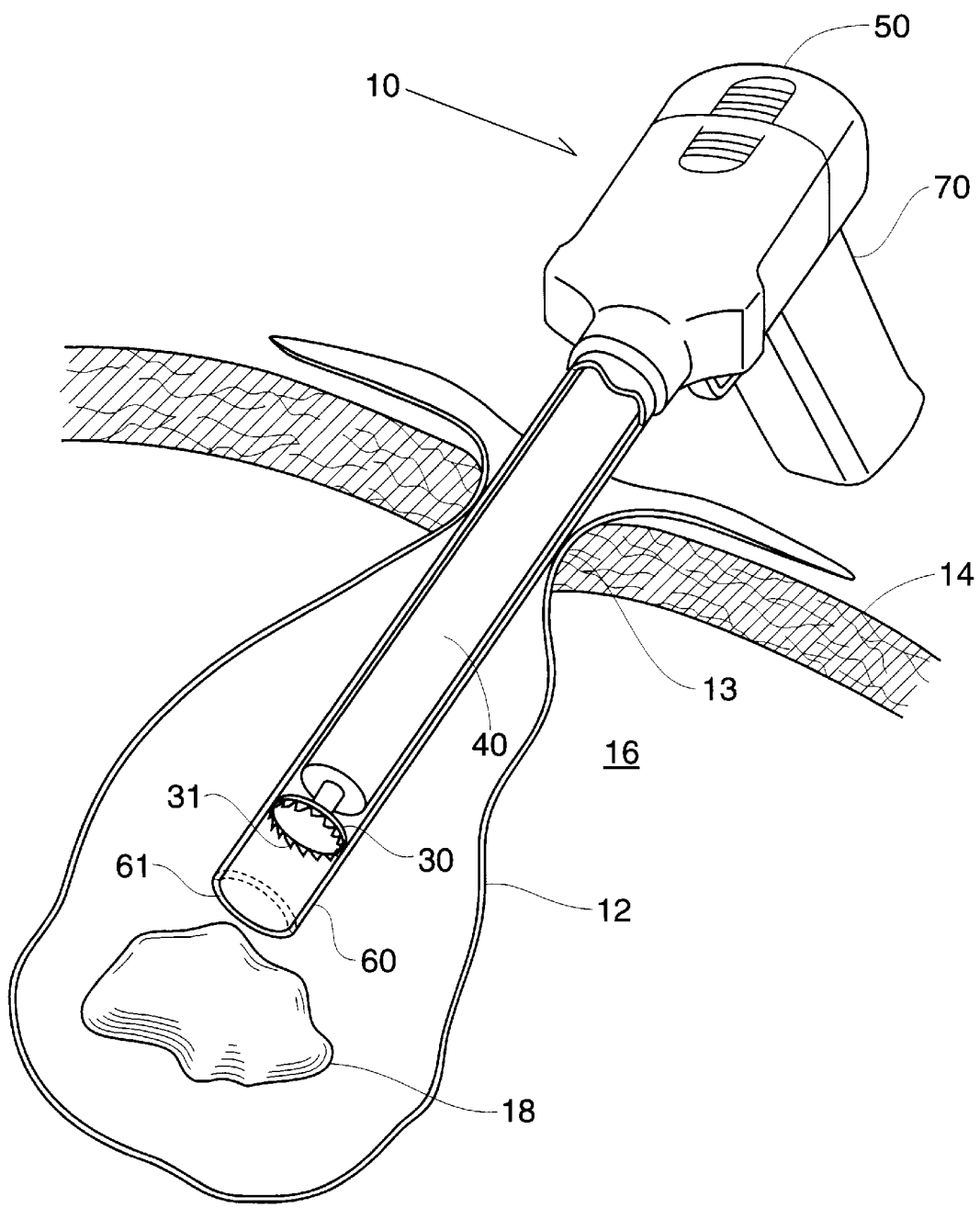
FIG. 1 is a perspective view of the present invention in use in a tissue retrieval bag in a body cavity.
Figure 2:
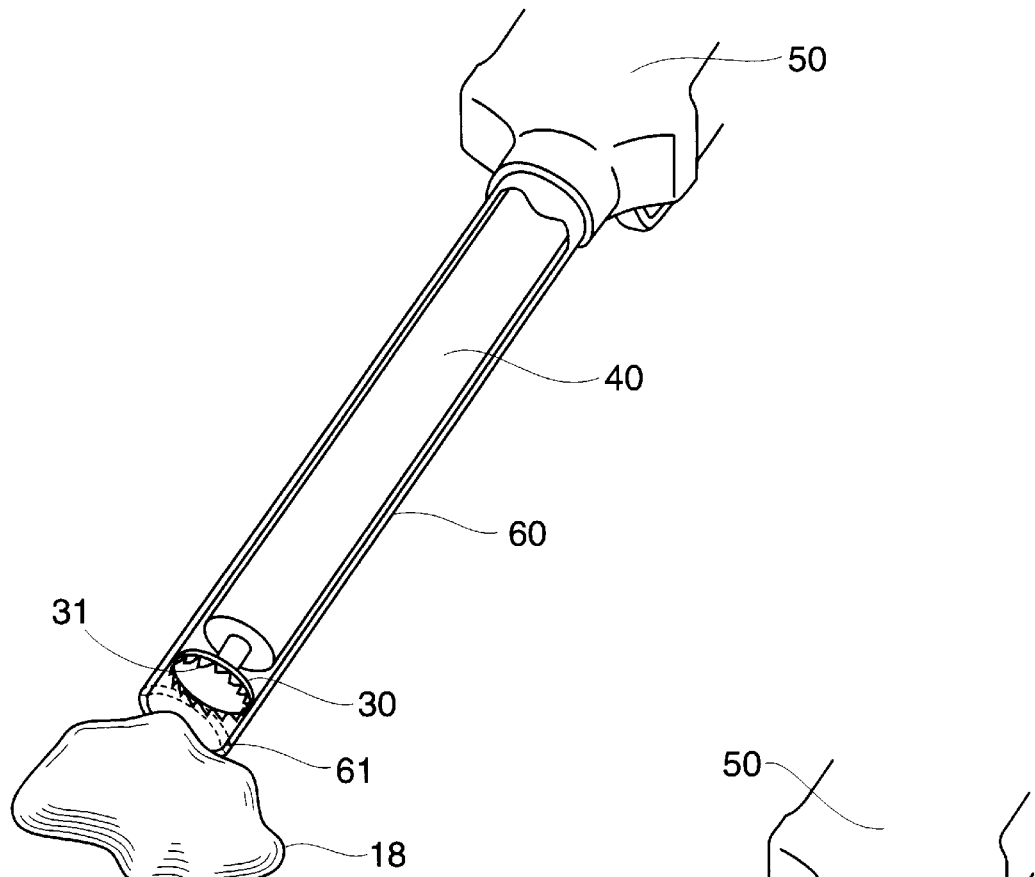
FIG. 2 is a perspective view of the present invention showing the protective structure extended over the cutting structure.
Figure 3:
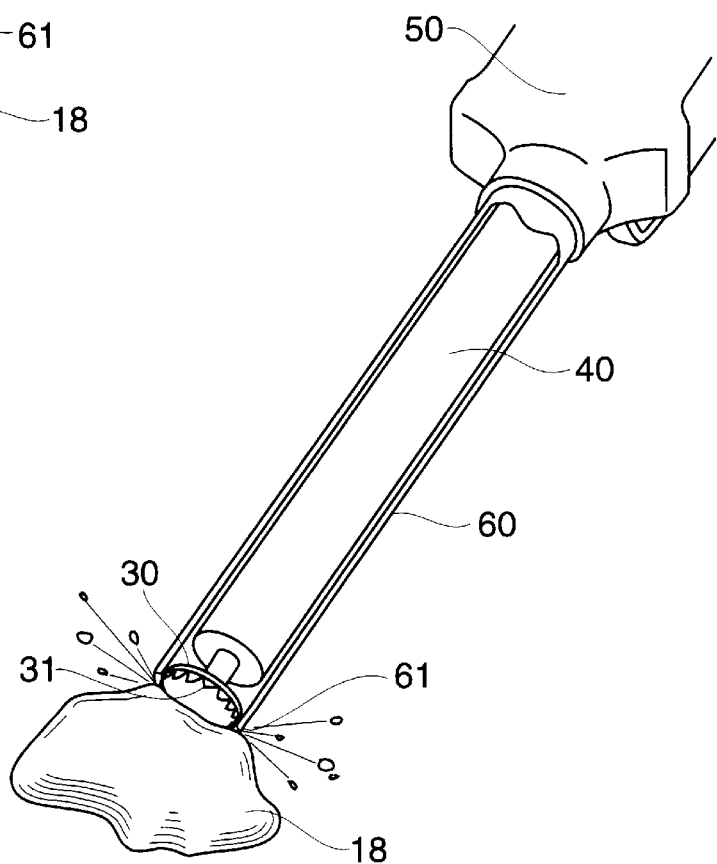
FIG. 3 is a perspective view of the present invention showing the protective structure partially retracted away from the cutting structure. The cutting structure engaging and cutting a predetermined tissue material.

Referring to FIGS. 1, 2, and 3 the theory of operation is illustrated. The bag 12 is shown already open and ready to receive the morcellater 10. The tissue or tumor material 18 is contained within the bag 12. The cutting hub 30, with the protective shield 60 extended around it, is extended into the bag 12. Distal end 61 of the protective shield 60 engages the target tissue 18. The resistance of the target tissue 18 overcomes the predetermined bias of the spring 90 so that the protective shield 60 retracts when distal end 61 is pressed against the target tissue 18. The total distance the spring 90 can compress is predetermined so that the protective shield 60 only retracts a predetermined distance sufficient to provide exposure of the cutting hub 30 sufficient for its cutting teeth 31 to engage the target tissue 18 so that it is cut or ground-up sufficiently and may be easily removed from the body cavity 16 by pulling the bag 12 through the small incision 13 in the body wall 14.

Should the pressure applied to the distal end 61 of the protective shield 60 be inadvertently reduced, e.g., due to slippage or other factors, the protective shield 60 will automatically be biased by the expansion pressure of the spring 90 to cover the cutting teeth 31 of the cutting hub 30 to prevent inadvertent damage to the bag 12 or the patient. Additionally, as illustrated by FIG. 7, the morcellater 10, while being provided with essentially three speeds between its high and low speed may have an infinite number of speeds between its high speed and its low speed. Also, optionally, the morcellater 10 may include a first off position located below its lowest speed and a second off position above its highest speed. This is so the operator may easily shut the morcellater's 10 motor 52 off by releasing the trigger 72. Additionally, the morcellater 10 may have its motor 52 shut off should the operator completely depress the trigger 72. This optional feature is provided as a means for disengaging the motor 52 if the surgeon operating the morcelator were to have a seizure.

Referring now to FIG. 6 an alternative embodiment of the morcellater 10 is shown. This embodiment illustrates that the drive cylinder 40 is an optional feature and that the present invention may be practiced without it. Accordingly, the alternative embodiment of FIG. 6 only requires the motor housing 50 containing a motor 52 having a receptacle 54 for receiving end 24 of drive shaft 20, drive shaft 20, a cutting hub 30, and protective shield 60. Further it should be understood in both embodiments specifically shown and in all embodiments claimed, without limitation, that receptacle 54 does not have to be threaded but may include other engagement structures, e.g., a collet or externally coned sleeve, slit in two or more planes for part of its length and arranged to be closed by being drawn into an internally coned rigid sleeve, for the purpose of gripping a structure like the drive shaft 20.

Figure 8:
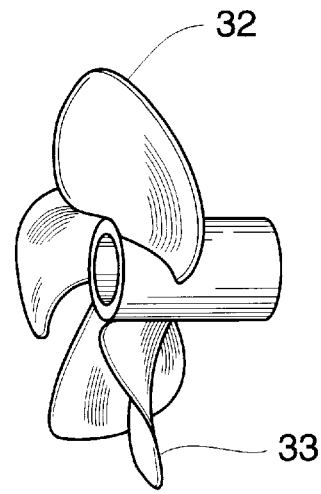
FIG. 8 shows an alternative cutting element structure.
Figure 9:
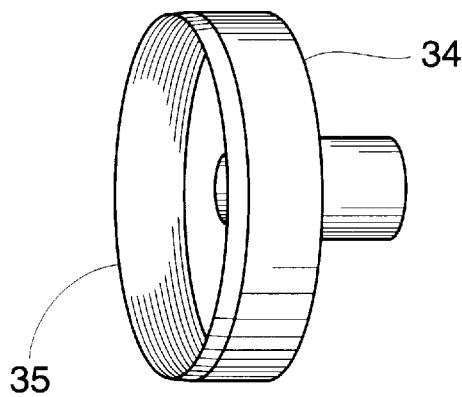
FIG. 9 shown another alternative cutting element structure.
Figure 10:
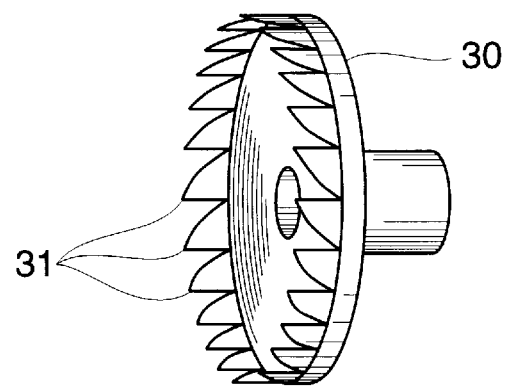
FIG. 10 shows the cutting element structure.

Finally, referring to FIGS. 8 and 9 at least two alternative cutting or grinding tools 32 and 34 are disclosed, respectively. In FIG. 8, grinding tool 32 is a propeller type structure having cutting props 33. In FIG. 9, grinding tool 34 includes a continuous cutting edge 35.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A morcellater comprising:

at least one cutting structure coupled to a motor mechanism;

said cutting structure having a protective structure circumjacent thereto;

said protective structure being slidably coupled to a housing structure wherein at least a portion of said motor mechanism is located.

2. The morcellater of claim 1 wherein said housing structure contains at least one biasing element.

3. The morcellater of claim 2 wherein said motor mechanism is a variable speed motor.

4. The morcellater of claim 2 wherein said protective structure includes a proximate end and said biasing element is engaged and biased against said proximate end.

5. The morcellater of claim 4 wherein said biasing element includes a first end biased against said proximate end and a second end biased against said motor.

6. The morcellater of claim 2 wherein the biasing element is a spring.

7. The morcellater of claim 1 wherein said protective structure is substantially cylindrical.

8. The morcellater of claim 1 wherein said protective structure includes a proximate end and said housing structure includes at lease one opening;

said proximate end slidably extending through said opening.

9. The morcellater of claim 1 including a drive shaft having a first end coupled to said motor and a second end coupled to said cutting structure.

10. The morcellater of claim 9 including a drive cylinder circumjacent said drive shaft.

11. The morcellater of claim 1 including a switching mechanism coupled to said motor;

said motor being actuated and controlled by said switching mechanism.

12. The morcellater of claim 11 wherein the switching mechanism has a first off position and a second off position;

said switching mechanism including at least one on position;

all said on positions located between said first off position and said second off position.

13. The morcellater of claim 1 wherein said protective structure includes at least one distal end having at least one opening;

said cutting structure capable of being extended a predetermined distance through said opening.

14. A method of using a morcellater in a body cavity through an incision made therein and wherein the morcellater includes at least one grinding structure, coupled to a motor mechanism, and a protective structure located circumjacent to said grinding mechanism; the protective structure having at least a first end coupled a housing structure wherein at least a portion of the motor mechanism is located and a second free end wherein the grinding structure is generally located; said first end able to freely, upon the application of a predetermined level of pressure to said free end, slide into and out of the housing at least a predetermined distance; the method comprising:

applying the free end of the protective structure against a target tissue mass;

applying sufficient force to cause the first end to slide into the housing a predetermined distance;

engaging the grinding structure with the target tissue; and actuating the motor mechanism to cause the grinding mechanism to grind up the target tissue sufficiently to allow its removal from the body cavity through said incision.

* * * * *